US00PP13160P2

(12) United States Plant Patent
Michalik

(10) Patent No.: US PP13,160 P2
(45) Date of Patent: Oct. 29, 2002

(54) VARIETY OF GERANIUM PLANT NAMED 'TIKPINK'

(75) Inventor: Andrea Michalik, Dresden (DE)

(73) Assignee: Elsner pac Jungplanzen (DE)

( * ) Notice: Subject to any disclaimer, the term of this patent is extended or adjusted under 35 U.S.C. 154(b) by 0 days.

(21) Appl. No.: 09/733,024

(22) Filed: Dec. 8, 2000

(65) Prior Publication Data

US 2002/0073463 P1 Jun. 13, 2002

(51) Int. Cl.[7] ..... A01H 5/00
(52) U.S. Cl. ..... Plt./329
(58) Field of Search ..... Plt./325, 328, 329

(56) References Cited

PUBLICATIONS

GTITM UPOVROM Citation for 'Tikpink' as per QZ PBR 981016; Jul. 23, 1998.

GTITM UPOVROM Citation for 'Tikpink' as per IL PBR 03094; Sep. 9, 1999.

*Primary Examiner*—Kent L. Bell
(74) *Attorney, Agent, or Firm*—Webb Ziesenheim Logsdon Orkin & Hanson, P.C.

(57) ABSTRACT

A new and distinct zonal geranium plant with intense pink colored flowers above medium green foliage. The plant is suitable for solitaire pot planting.

1 Drawing Sheet

BOTANICAL/COMMERCIAL CLASSIFICATION

*Pelargonium×hortorum*; Zonal Geranium.

VARIETY DENOMINATION

'Tikpink'.

BACKGROUND OF THE INVENTION

The present invention comprises a new and distinct cultivar of *Pelargonium×hortorum* known by the varietal name 'Tikpink'. The new variety was discovered in 1996 in a selective breeding program in Dresden, Germany. The new variety is the result of a combination breeding of 60 unpatented, unnamed seedlings having pink colored flowers. The flower color of 'Tikpink' is less intense than its pollen parent, and the growth vigor is less than its seed parent. The new variety was first asexually reproduced by cuttings in Dresden, Germany in 1997. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these charaterictics were collected by asexual reproductions by cuttings carried out in Dresden, Germany. The color readings were taken outdoors in shadow during summer on a 9 month old plant grown in a 19 cm pot. Color references are primarily to The R.H.S. Colour Chart of The Royal Horticultural Society of London.

PLANT

Form: Erect.
Overall height: 120 cm after 1 year.
Height from media surface to top of foliage: 70 cm after 6 months.
Height from media surface to top of umbel: 65–70 cm after 6 months.
Width: 40 cm after 9 months.
Growth: Erect.
Strength: Requires support.
Response time: 4 weeks.
Leaves:
- *Size.*—6.0–8.0 cm long; 6.0–8.0 cm wide.
- *Shape.*—Cordate.
- *Margin.*—Crenate.
- *Texture.*—Hairy.
- *Color.*—Upper side is Green Group 137A with prominent zone of Greyed-Orange Group 166A; lower side is Green Group 138A.
- *Veins.*—Green Group 138B.

Petioles:
- *Color.*—Green Group 138B.
- *Length.*—7.0–9.0 cm.
- *Diameter.*—2 mm.

Stem/branches:
- *Color.*—Green Group 137D.
- *Internode length.*—3.0–5.0 cm.

THE BUD

Shape when just showing color:
- *Overall.*—Semi-spherical.
- *Individual bud.*—Narrow; elliptical.

Color: Yellow-Green Group 144A.
Size when just showing color:
- *Umbel.*—8.0–10.0 cm across.
- *Individual bud.*—1.5 cm long; 1.0 cm wide.

INFLORESCENCE

Blooming habit: Single; 140 blooms per flowering season of spring until frost.
Size of fully open umbel: 7–9 cm in diameter; 5 cm deep.
Borne: Umbel; flowers on pedicel; pedicel on peduncle.
Flowers:
*Form*.—Zygomorph.
*Number of petals*.—5.
*Size*.—2.0 cm wide; 2.5 cm long.
*Petals*.—Color: Red-Purple Group 66C on upper and lower surfaces. Shape: Round apex; pointed base; entire margin.
*Texture and appearance*.—Velvety.
Petaloids: Absent.
Sepals:
*Quantity*.—5.
*Size*.—3 mm wide; 7 mm long.
*Shape*.—Pointed apex; wide base; entire margin.
*Color*.—Green Group 138A on upper and lower surfaces.
Pedicel:
*Length*.—2.5–3.0 cm.
*Color*.—Green Group 137B.
Peduncle:
*Length*.—11.0–13.0 cm.
*Color*.—Green Group 137B.
Disease/pest resistance: No susceptibility to diseases or pests has been noted to date.
Lasting quality: Semi-long-lasting; 2 weeks per umbel.

REPRODUCTIVE ORGANS

Stamens:
*Anthers*.—3 mm long.
*Filaments*.—Length: 0.5 cm maximum. Color: Pink.
*Pollen*.—Yellow.
Pistils:
*Number*.—One, five parted.
*Length*.—0.3–0.4 cm.
*Stigma*.—Pink.
*Style*.—0.8 cm long.
Ovaries:
*Color*.—Greenish.
*Length*.—0.4 cm.
Fruit: Produces 18–25 fruits per inflorescence colored Greyed-Orange Group 166A with 5 seeds per fruit on one column 3–4 cm long and 5 mm wide.

GENERAL CHARACTERISTICS

1. Suitable for solitaire pot plant.
2. Must be bound to get a pyramid shape.
3. Pinched several times for groundcover.
4. Very decorative.
5. Long-lasting.

I claim:

1. A new and distinct variety of geranium plant substantially as shown and described.

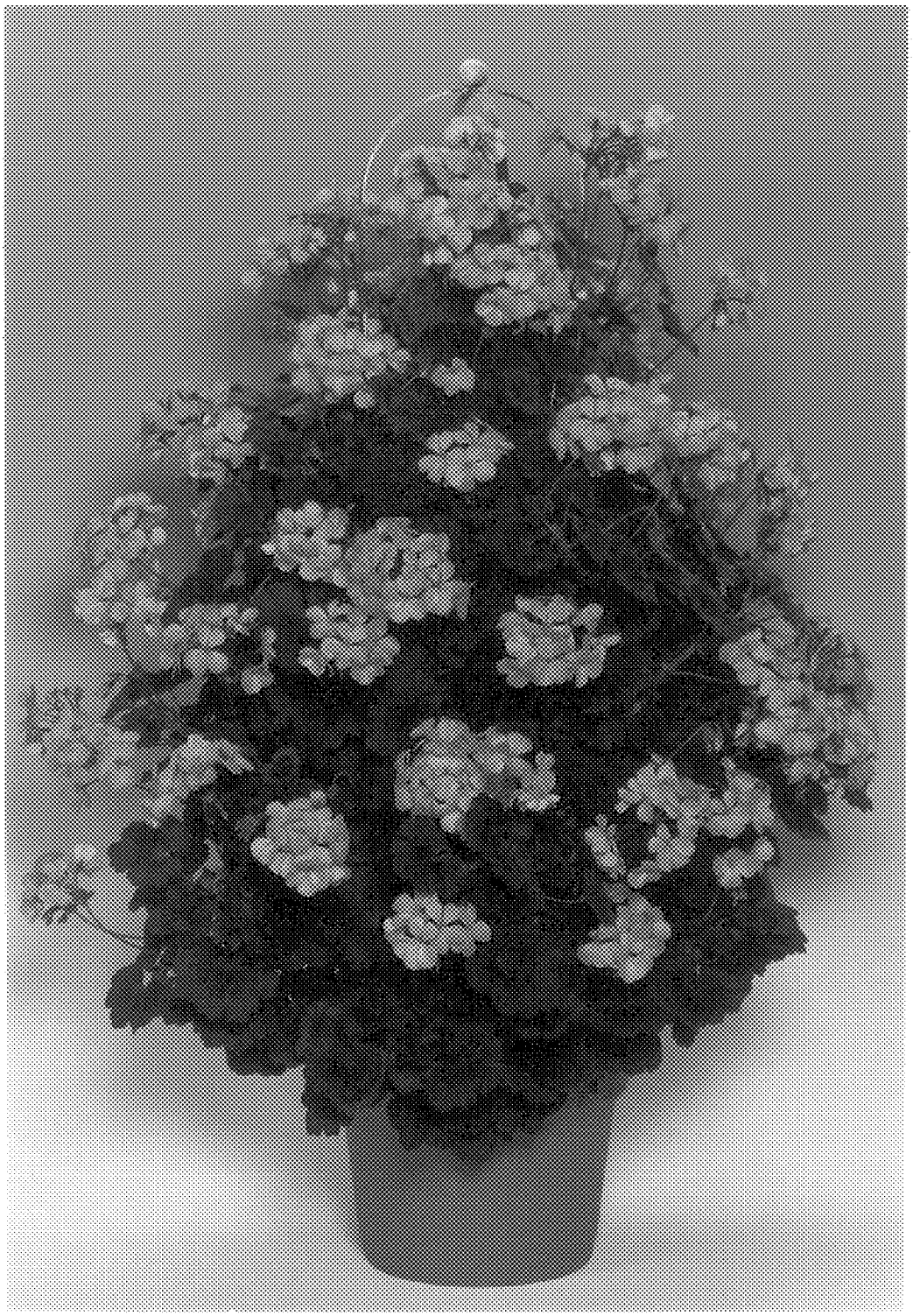

* * * * *